United States Patent
Masuda et al.

(10) Patent No.: US 8,677,804 B2
(45) Date of Patent: *Mar. 25, 2014

(54) CONTACT MEMBER FOR GAS SENSOR, GAS SENSOR, CONSTRAINT MEMBER, CONNECTING METHOD OF SENSOR ELEMENT AND CONTACT MEMBER OF GAS SENSOR, MANUFACTURING METHOD OF GAS SENSOR

(75) Inventors: Koichi Masuda, Nagoya (JP); Hirohito Kiyota, Kiyosu (JP); Nobukazu Ikoma, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/442,151

(22) Filed: Apr. 9, 2012

(65) Prior Publication Data

US 2012/0192653 A1    Aug. 2, 2012

Related U.S. Application Data

(63) Continuation of application No. PCT/JP2010/067445, filed on Oct. 5, 2010.

(30) Foreign Application Priority Data

Oct. 13, 2009    (JP) .................. 2009-235864

(51) Int. Cl.
    *H01R 4/26*    (2006.01)

(52) U.S. Cl.
    USPC ........... 73/31.05; 204/424; 439/263; 439/435

(58) Field of Classification Search
    USPC .......... 73/31.05; 439/263, 345, 346; 204/424, 204/426
    See application file for complete search history.

(56) References Cited

U.S. PATENT DOCUMENTS

| | | | | |
|---|---|---|---|---|
| 4,983,271 A | * | 1/1991 | Kato et al. | 204/426 |
| 5,556,526 A | * | 9/1996 | Fukaya et al. | 204/425 |
| 6,527,573 B2 | * | 3/2003 | Stein et al. | 439/260 |
| 6,672,136 B2 | * | 1/2004 | Kojima | 73/31.05 |

(Continued)

FOREIGN PATENT DOCUMENTS

| | | |
|---|---|---|
| JP | 04-110972 U | 9/1992 |
| JP | 11-248671 A1 | 9/1999 |
| JP | 2001-343356 A1 | 12/2001 |
| JP | 2004-093306 A1 | 3/2004 |
| JP | 2006-284223 A1 | 10/2006 |
| JP | 2009-115784 A1 | 5/2009 |

OTHER PUBLICATIONS

International Search Report dated Nov. 30, 2010.

*Primary Examiner* — Lisa Caputo
*Assistant Examiner* — Punam Roy
(74) *Attorney, Agent, or Firm* — Burr & Brown, PLLC (57) ABSTRACT

To provide a gas sensor which can stably carry out a securement of an electric continuity between a sensor element and a contact member. A contact member in which an electric connection to a sensor element is obtained by pinching and fixing the sensor element in an inserting port formed by a pair of housing members includes a constraint member which is provided in an outer periphery of a pair of housing members. The constraint member constrains a displacement of a pair of housing members within a predetermined range before the sensor element is pinched and fixed by a pair of housing members, and exists in a state of being pinched between the annular member and a pair of housing member without generating any reaction force with respect to the external force, after the sensor element is pinched and fixed.

6 Claims, 10 Drawing Sheets

(56) References Cited

U.S. PATENT DOCUMENTS

| | | | |
|---|---|---|---|
| 7,425,138 B2* | 9/2008 | Buhl et al. | 439/76.1 |
| 7,798,855 B2* | 9/2010 | Gustin | 439/620.01 |
| 8,287,294 B2* | 10/2012 | Masuda et al. | 439/260 |
| 2001/0025522 A1 | 10/2001 | Kojima | |
| 2004/0040370 A1 | 3/2004 | Kojima | |
| 2009/0101503 A1 | 4/2009 | Kanao | |
| 2009/0156045 A1* | 6/2009 | Gustin | 439/345 |
| 2012/0071042 A1* | 3/2012 | Masuda et al. | 439/890 |
| 2012/0216599 A1* | 8/2012 | Kitoh | 73/31.05 |

* cited by examiner

CONTACT MEMBER FOR GAS SENSOR, GAS SENSOR, CONSTRAINT MEMBER, CONNECTING METHOD OF SENSOR ELEMENT AND CONTACT MEMBER OF GAS SENSOR, MANUFACTURING METHOD OF GAS SENSOR

BACKGROUND OF THE INVENTION

1. Field of the Invention

The present invention relates to a gas sensor for measuring a concentration of a predetermined gas component in a measurement gas, and more particularly to a technique of retaining and fixing a sensor element thereof.

2. Description of Related Art

Conventionally, in order to know a concentration of a desired gas component in a measurement gas, there have been known various measuring apparatuses. For example, as an apparatus which measures an NOx concentration in the measurement gas such as a combustion gas or the like, there has been known a gas sensor (an NOx sensor) having an oxygen ion conductivity such as a zirconia ($ZrO_2$) or the like (for example, refer to Japanese Patent Application Laid-Open No. 2006-284223 (patent document 1)). The sensor element of the gas sensor mentioned above typically has a plurality of electrode terminals on a surface for applying an electric voltage, picking up a detection signal, supplying an electric power to a heater part and the like.

On the other hand, the gas sensor is provided with a contact member in which the sensor element is inserted so as to retain. For example, there has already known a gas sensor having a contact member which is provided with a housing forming an insertion port in which the sensor element is inserted by a pair of housing members arranged so as to be opposed to each other, a plurality of contact point members which are additionally provided in the housing members and constructed by metal terminals, and a plurality of lead wires which are connected to the contact point members and achieve an electric continuity between the sensor element and an external portion (for example, refer to Japanese Utility Model Application Laid-Open No. 4-110972 (patent document 2)).

In the gas sensor disclosed in Japanese Utility Model Application Laid-Open No. 4-110972, the contact member retains the sensor element which is inserted in an insertion port, in a state that the contact point member is brought into contact with the electrode terminal, thereby obtaining the electric continuity between the sensor element and the external portion. In other words, in the gas sensor disclosed in Japanese Utility Model Application Laid-Open No. 4-110972, the contact point member plays a role in a contact point with the electrode terminal. Specifically, housing members are fitted into a fixing metal fixture having a C-shaped form in a cross sectional view with the pressing spring in its upper and lower sides, while the sensor element is inserted in the insertion port therebetween, and then, a caulking ring is arranged in an outer periphery of the fixing metal fixture and the pressing spring and is caulked so that the spring ring is displaced to energize the contact point member to the electrode terminal with an elastic force of the pressing spring. Thus, a retention of the sensor element and a preservation of the electric continuity are achieved.

The fixing metal fixture disclosed in Japanese Utility Model Application Laid-Open No. 4-110972 not only has a role for fixing the spring member as mentioned above, but also has a role for constraining a pair of housing members in a predetermined arrangement relationship as long as the sensor element is inserted and the caulking ring is caulked. The constraint mentioned above is necessary for correctly bringing the electrode terminal into contact with the corresponding contact point member without any displacement, at a time of retaining and fixing the sensor element to the contact member between a pair of housing members (that is, in the insertion port) by caulking the caulking ring. In the case of Japanese Utility Model Application Laid-Open No. 4-110972, by forming the fixing metal fixture in the C-shaped form in the cross section, its elasticity as a leaf spring is utilized for retaining and constraining the housing member.

In the gas sensor disclosed in Japanese Utility Model Application Laid-Open No. 4-110972, the elastic force of the pressing spring acts on the housing via the fixing metal fixture with the caulking ring being caulked, whereby the sensor element is fixed to the housing. At this time, the contact point member provided in the housing energizes the electrode terminal, whereby a contact between the electrode terminal and the contact point member is secured.

However, at that time, since the fixing metal fixture has the C-shaped form in the cross section as mentioned above, there is such a problem that a force acting on the housing comes to have an asymmetry (a nonuniformity). In the gas sensor structured such that a plurality of electrode terminals come into contact with the corresponding contact point members, the force with which each of contact point members energizes the electrode terminal differs according to its position, because of such nonuniformity. As a result, a local contact failure is likely to occur.

SUMMARY OF THE INVENTION

The present invention is made by taking the problem mentioned above into consideration, and an object of the present invention is to provide a gas sensor which can stably carry out a securement of an electric continuity between a sensor element and a contact member.

In order to solve the above problems, a first aspect of the present invention provides a contact member for a gas sensor in which an electric connection to a sensor element is obtained by pinching and fixing the sensor element in an inserting port formed by a pair of housing members, including: a constraint member which is provided in an outer periphery of the pair of housing members and has a constraining function of constraining a displacement of the pair of housing members within a predetermined range; and an annular member which is provided in an outer periphery of the constraint member, wherein the pair of housing members and the sensor element are brought into pressure contact, and the sensor element is pinched and fixed by the pair of housing members in a state that an electrode terminal provided in the sensor element comes into contact with a contact point member provided in the pair of housing members, due to contractive deformation of the annular member with receiving an external force in a state that the sensor element is inserted in the insertion port, and the constraint member constrains a displacement of the pair of housing members within a predetermined range before the sensor element is pinched and fixed by the pair of housing members, and exists in a state of being pinched between the annular member and the pair of housing member without generating any reaction force with respect to the external force, after the sensor element is pinched and fixed.

In a second aspect of the present invention, in the contact member for the gas sensor according to the first aspect, the constraint member is constructed by a first member and a second member, and the engagement of the first member and the second member causes the constraint of the pair of housing members with the constraint member.

In a third aspect of the present invention, in the contact member for the gas sensor according to the second aspect, the constraint member is provided with two sets of engaging mechanisms which engage the first member and the second member, and each of the two sets of engaging mechanisms is constructed by an engaging part which is provided in one of the first member and the second member and an engaged part which is provided in the other.

In a fourth aspect of the present invention, in the contact member for the gas sensor according to the third aspect, wherein each of the first member and the second member is provided with the engaging part and the engaged part of the two sets of engaging mechanisms one by one.

In a fifth aspect of the present invention, in the contact member for the gas sensor according to the fourth aspect, the first member and the second member are members having approximately the same shape.

In a sixth aspect of the present invention, in the contact member for the gas sensor according to the third aspect, the engaging parts of both of the two sets of engaging mechanisms are provided in one of the first member and the second member, and the engaged parts of both of the two sets of engaging mechanisms are provided in the other of the first member and the second member.

A seventh aspect of the present invention provides a connecting method of a sensor element of a gas sensor and a contact member, including: a step of preparing a contact member that includes a pair of housing members which are arranged to form an insertion port in which the sensor element is inserted, a constraint member which is provided in an outer periphery of the pair of housing members, and has a constraining function of constraining a displacement of the pair of housing members within a predetermined range, and an annular member which is provided in an outer periphery of the constraint member; a step of inserting the sensor element in the insertion port; and a step of bringing the pair of housing members into pressure contact with the sensor element by applying an external force to the annular member to deform the annular member so as to contract, thereby pinching and fixing the sensor element in the pair of housing members in a state that an electrode terminal provided in the sensor element is brought into contact with a contact point member provided in the pair of housing members, wherein the constraint member constrains a displacement of the pair of housing members within a predetermined range before the sensor element is pinched and fixed by the pair of housing members, and exists in a state of being pinched between the annular member and the pair of housing members without generating any reaction force with respect to the external force, after the sensor element is pinched and fixed.

In an eighth aspect of the present invention, in the connecting method of the sensor element of the gas sensor and the contact member according to the seventh aspect, the constraint member is constructed by a first member and a second member, and the engagement of the first member and the second member causes the constraint of the pair of housing members with the constraint member.

In a ninth aspect of the present invention, in the connecting method of the sensor element of the gas sensor and the contact member according to the eighth aspect, the constraint member is provided with two sets of engaging mechanisms which engage the first member and the second member, and each of the two sets of engaging mechanisms is constructed by an engaging part which is provided in one of the first member and the second member and an engaged part which is provided in the other.

A tenth aspect of the present invention provides a manufacturing method of a gas sensor including: a step of arranging a pair of housing members in a state of forming an inserting port in which a sensor element is inserted; a step of providing a constraint member having a constraining function of constraining a displacement of the pair of housing members within a predetermined range, in an outer periphery of the pair of housing members; a step of providing an annular member in an outer periphery of the constraint member; a step of inserting the sensor element in the insertion port; and a step of bringing the pair of housing members into pressure contact with the sensor element by applying an external force to the annular member to deform the annular member so as to contract, thereby pinching and fixing the sensor element in the pair of housing members in a state that an electrode terminal provided in the sensor element is brought into contact with a contact point member provided in the pair of housing members, wherein the constraint member constrains a displacement of the pair of housing members within a predetermined range before the sensor element is pinched and fixed by the pair of housing members, and exists in a state of being pinched between the annular member and the pair of housing members without generating any reaction force with respect to the external force, after the sensor element is pinched and fixed.

In an eleventh aspect of the present invention, in the manufacturing method of the gas sensor according to the tenth aspect, the constraint member is constructed by a first member and a second member, and the engagement of the first member and the second member causes the constraint of the pair of housing members with the constraint member.

In a twelfth aspect of the present invention, in the manufacturing method of the gas sensor according to the eleventh aspect, the constraint member is provided with two sets of engaging mechanisms which engage the first member and the second member, and each of the two sets of engaging mechanisms is constructed by an engaging part which is provided in one of the first member and the second member and an engaged part which is provided in the other.

In accordance with the first to twelfth aspect of the present invention, since it is possible to securely achieve a uniform and stable contact state between the contact point member provided in the housing member and the electrode terminal of the sensor element, it is possible to a more stable electric connection than the conventional one between the sensor element and the contact member.

Particularly, in accordance with the second to eighth, eleventh and twelfth aspects, since it is possible to more securely prevent a generation of a reaction force with respect to an external force which is applied for deforming the annular member so as to contract, it is possible to obtain more securely achieve the uniform and stable contact state between the contact point member provided in the housing member and the electrode terminal of the sensor element.

DETAILED DESCRIPTION OF THE INVENTION

<Outline Structure of Gas Sensor>

Figure 1A:
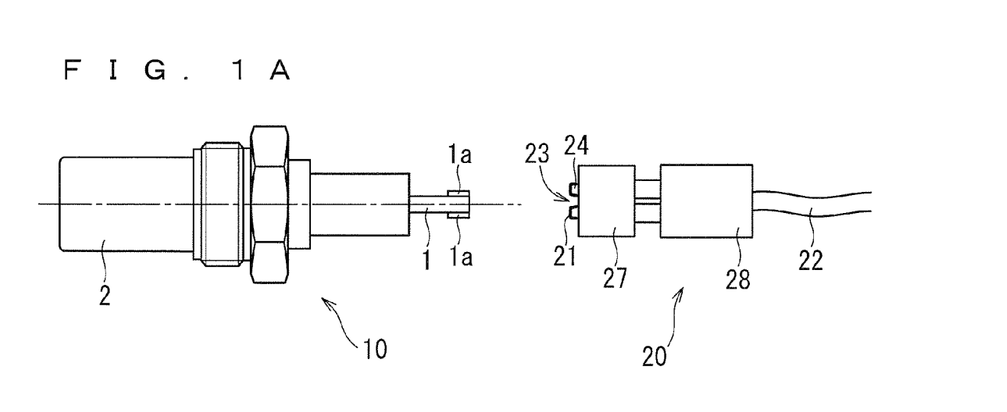
FIGS. 1A and 1B are views showing a situation at a time of assembling a gas sensor 100.
Figure 1B:
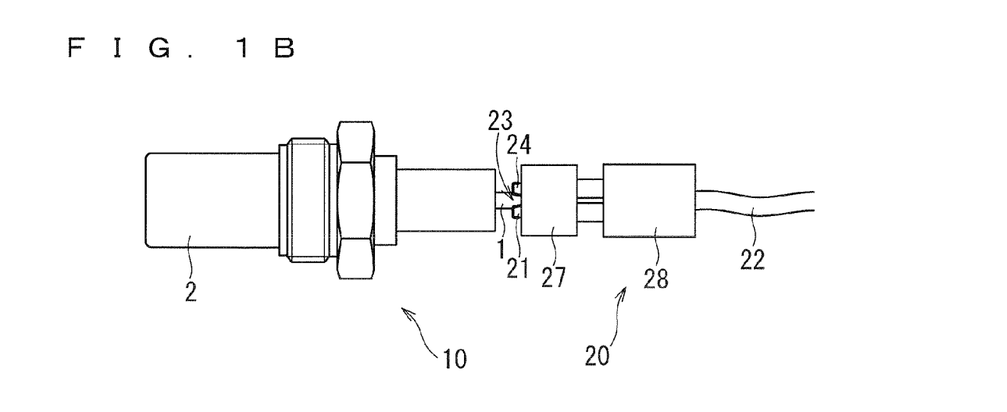

First of all, a description will be given of an outline structure of a gas sensor 100. The gas sensor 100 is structured such as to detect a predetermined gas component (a target gas component) in a gas that is a measuring target (a measurement gas), and measure a concentration thereof. FIGS. 1A and 1B are views showing a situation at a time of assembling the gas sensor 100. FIG. 1A shows a situation before the assembling, and FIG. 1B shows a situation after the assembling.

The gas sensor 100 has a structure in which a gas sensor main body 10 and a contact member 20 are integrated. The gas sensor main body 10 is provided with a sensor element 1 which is a gas detector, and an accommodating member 2 which accommodates the sensor element 1. On the other hand, the contact member 20 is mainly provided with a plurality of contact point members 21, a lead wire 22 which is connected to the contact point members 21, a housing 24 which is made of a ceramic and where the sensor element 1 is fitted in its insertion port 23 via the contact point members 21 so as to be retained, and a grommet 28 which is formed in such a manner that the lead wire 22 can be inserted inside thereof in an airtight manner.

As shown in FIG. 1B, the sensor element 1 provided in the gas sensor main body 10 is inserted to the insertion port 23 of the housing 24 provided in the contact member 20, and the sensor element 1 is retained in the housing 24 via the contact point members 21, whereby the gas sensor 100 is integrated.

Figure 2:
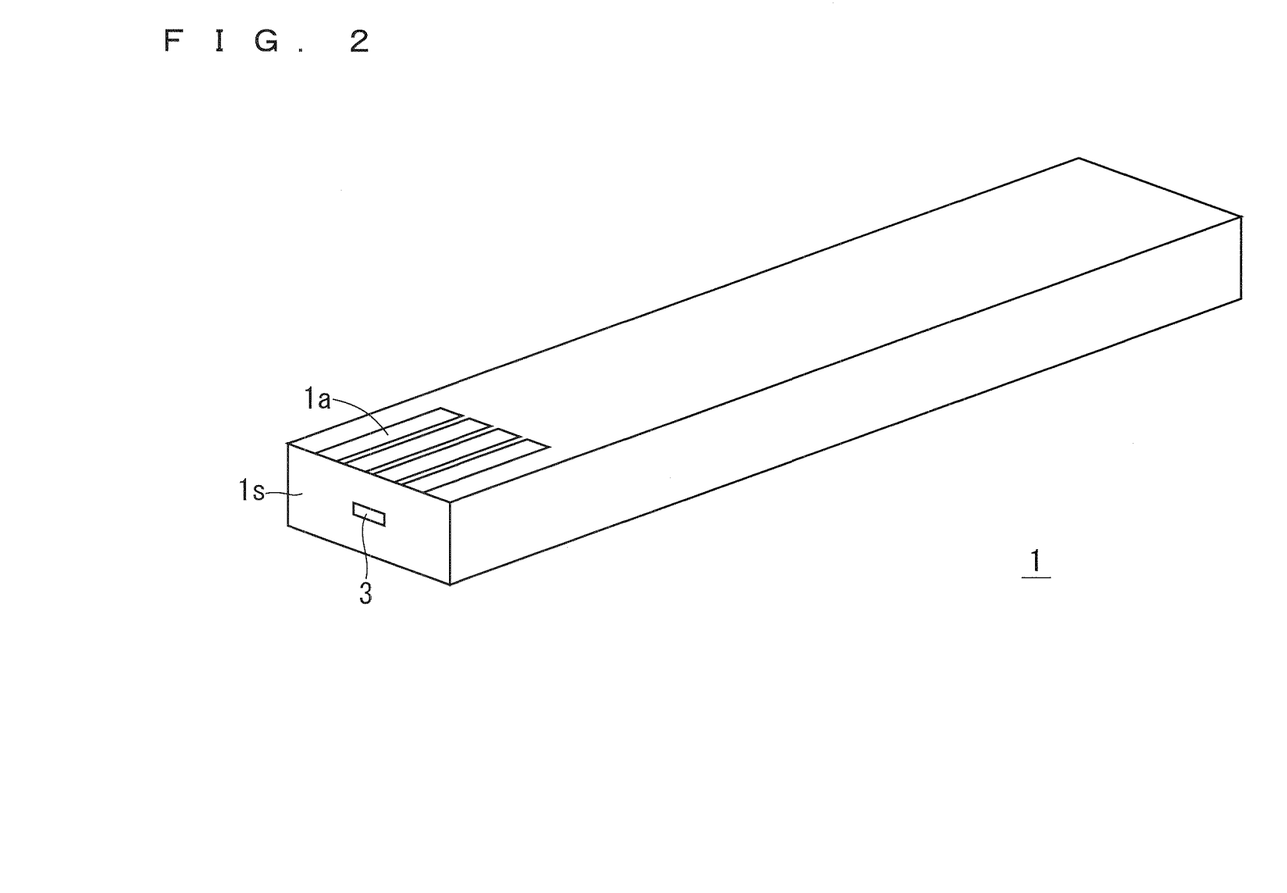
FIG. 2 is a perspective view showing an outer shape of a sensor element 1.

FIG. 2 is a perspective view showing an outer shape of the sensor element 1. The sensor element 1 has a structure in which a plurality of layers are laminated, each of which is constructed by an oxygen ion conducting solid electrolyte such as a zirconia ($ZrO_2$) or the like. Further, front and back surfaces of the sensor element 1 are provided with a plurality of electrode terminals 1a for applying an electric voltage, picking up a detected signal, supplying an electric power to a heater part and the like. In FIG. 2, there is illustrated the sensor element 1 in which four electrode terminals 1a are provided in one surface (an illustration of the electrode terminals 1a in the back surface side is omitted), however, this is just an exemplification, and the number of the electrode terminals 1a can be appropriately determined in accordance with the structure of the sensor element 1. Further, the sensor element 1 has a gas introduction port 3 introducing a reference gas in an end surface is in a side where the electrode terminal 1a is provided, and is provided with a measurement gas introduction port which is not illustrated, in another end portion.

The sensor element 1 is manufactured, for example, by carrying out following steps: performing a predetermined processing and printing electrodes and wiring patterns on ceramics green sheets each corresponding to each of the layers of the sensor element 1, thereafter laminating them and cut in a predetermined magnitude, and burning the obtained laminated body. In the gas sensor 100, the target gas component is detected by utilizing a matter that an electric current corresponding to an abundance of the target gas component in the measurement gas flows between the predetermined electrodes provided inside at a time when the measurement gas is introduced to the sensor element 1.

<Detailed Structure of Contact Member>

Figure 3:
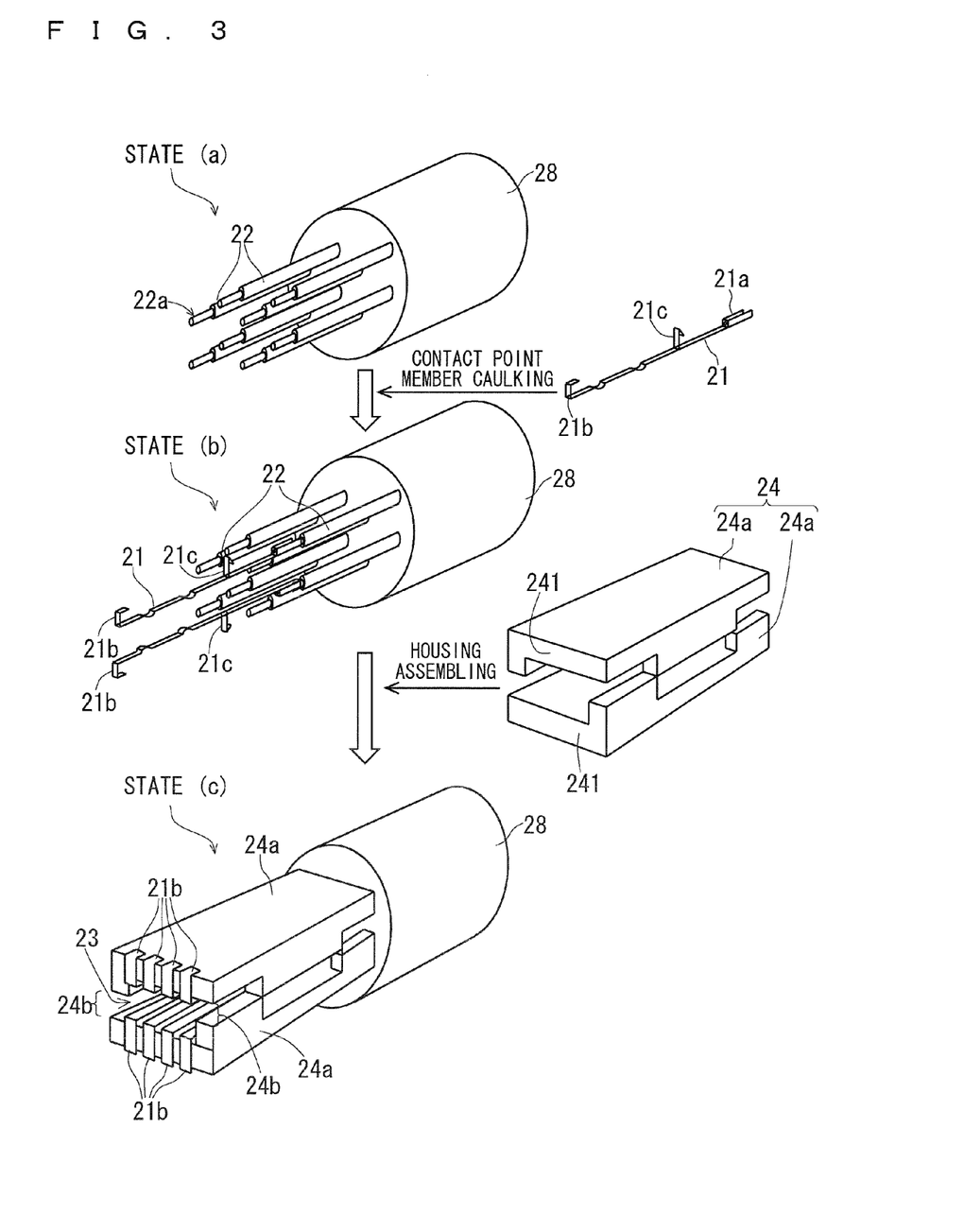
FIG. 3 is a view schematically showing an assembling process of a contact member 20.
Figure 4:
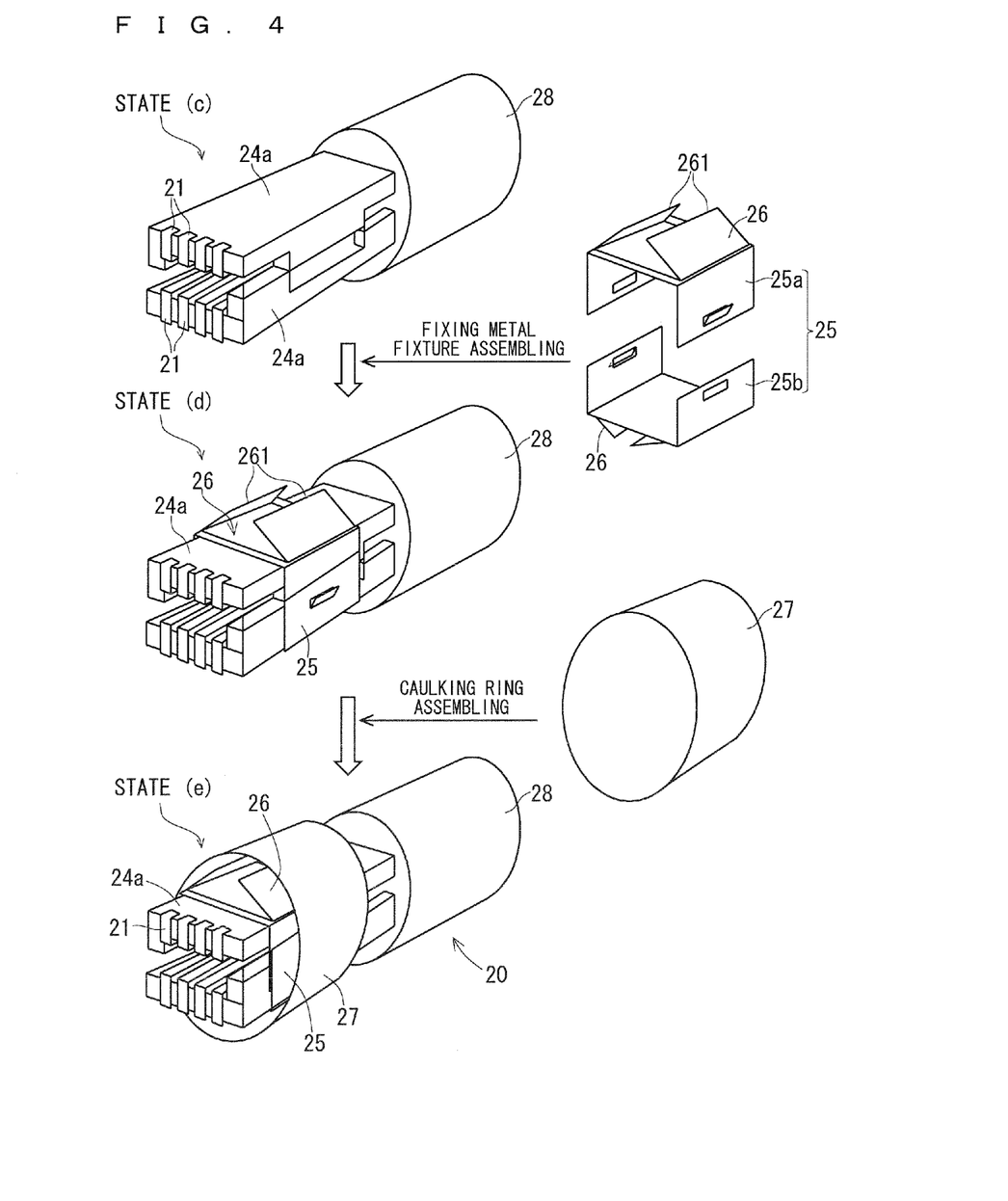
FIG. 4 is a view schematically showing the assembling process of the contact member 20.

Next, a description will be given of a detailed structure of the contact member 20 by showing an assembling process thereof. FIG. 3 and FIG. 4 are views schematically showing the assembling process of the contact member 20. In the sense of being previously carried out prior to the integration of the gas sensor main body 10 and the contact member 20, the assembling process of the contact member 20 is called as "preliminary assembling process", and the assembly is called as "preliminary assembly".

In the preliminary assembly of the contact member 20, first of all, as shown as a state (a) in FIG. 3, the lead wire 22 is inserted to the grommet 28. Next, as shown as a state (b), a crimp part 21a of the contact point member 21 is connected to an end part 22a of the lead wire 22. The connection is achieved by caulking the crimp part 21a from its outer side with the end part 22a of the lead wire 22 pinched to the crimp part 21a. In a state (b), there is exemplified a case that the contact point members 21 are connected only to two lead wires 22 for simplifying an illustration, however, the contact point members 21 are practically connected to all the lead wires 22.

After the contact point members 21 are connected, the housing 24 is next assembled as shown as a state (c). In more detail, the housing 24 is constructed by a pair of housing members 24a which are arranged so as to be opposed to each other, and a first attaching part 21b and a second attaching part 21c provided in the respective contact point members 21 are attached to predetermined positions of the housing member 24a, whereby an assembly of the housing 24 is achieved.

Specifically, the first attaching part 21b is attached to a first attached part 241 which is provided in one end part of the housing member 24a. Accordingly, the shapes of the first attaching part 21b and the first attached part 241 are defined in a manner that such attaching state can be well maintained. That is, the first attaching part 21b is processed to have a shape which is along a side cross sectional shape of the first attached part 241. On the other hand, the second attaching part 21c is attached to the housing member 24a by being inserted and fitted to a second attached part (not shown) provided in a center part of the housing member 24a.

In this case, the respective housing members 24a have approximately the same cross sectional shape, at a time of assembling, and are set to a mutually spaced state so that a space having a rectangular shape in a cross sectional view serving as the insertion port 23 is formed between both the members. In accordance with this, gaps 24b are provided in end parts of two housing members 24a. In other words, the housing member 24a can be said to have such a shape that housing 24 having a space inside and formed as a rectangular shape in a cross sectional view is divided into two pieces. By being assembled in the aspect mentioned above, when each of housing members 24a receives an external force in a vertical direction in the drawing view of FIG. 3 from inside of the insertion port 23, the vicinity of an end part of each of housing members 24a (adjacent to an end part of the insertion port 23) can deviate upward or downward within a certain range. Thus, when this pair of housing members 24a receiving the external force pinches the sensor element 1 in the insertion port 23, the sensor element 1 is fixed to the contact member.

At a time of assembling the housing 24, as shown as a state (d) in FIG. 4, a fixing metal fixture 25 to which a pressing spring 26 is previously fixed is assembled on an outer side of the housing 24 concurrently.

The pressing spring 26 is a leaf spring member which is formed as a trapezoidal shape without an upper base part in a cross sectional view, and generates an elastic force if an external force acts on a free end part 261 thereof, as its restoring force.

The fixing metal fixture 25 has a role for fixing the pressing spring 26, and has a role for maintaining an assembled state of the housing 24, more particularly, a state in which the insertion port 23 is formed, while the sensor element 1 is pinched and fixed. In other words, the fixing metal fixture 25 is a constraint member which constrains a pair of housing members 24a within a predetermined arrangement range so that the formation of the insertion port 23 is kept. By assembling the fixing metal fixture 25 together with the housing 24, a displacement between each of the contact point members 21 of the sensor element 1 and the corresponding electrode terminal 1a is prevented from occurring, at a time when the sensor element 1 is fixed. In other words, it can be said that the fixing metal fixture 25 has a role for constraining the arrangement range of the sensor element 1 at a time of pinching and fixing.

The gas sensor 100 according to the present embodiment is characterized in that the fixing metal fixture 25 is constructed by combining a first fixture member 25a and a second fixture member 25b. Details of the fixing metal fixture 25 will be mentioned later.

If the fixing metal fixture 25 is assembled, a caulking ring 27 which is an annular (a cylindrical) member is assembled, as shown as a state (c). In accordance with the above, the preliminary assembly is finished. In other words, the state (e) shows a state after the contact member 20 is assembled.

The caulking ring 27 is caulked in a state that the sensor element 1 is inserted in the insertion port 23 of the housing 24 at a time of integrating the gas sensor main body 10 and the contact member 20, after the preliminary assembly. In other words, the caulking ring 27 is deformed to shrink by an external force. In accordance with this, a clearance of the insertion port 23 of the housing 24 is narrowed, and the sensor element 1 is energized from two of upper and lower directions by the contact point member 21 provided in each of the housing members 24a. In other words, a state that the sensor element 1 is pinched and fixed by a pair of housing members 24a is achieved. At this time, since each of the contact point members 21 comes into contact with the corresponding electrode terminal 1a, an electric continuity between the sensor element 1 and the exterior is achieved via the lead wire 22 which is connected to the contact point member 21.

<Fixing Metal Fixture>

The present embodiment is characterized in that the fixing metal fixture 25 is constructed by a combination of the first fixture member 25a and the second fixture member 25b. A description will be given below of an operation and effect by employing the structure mentioned above, in addition to a specific description of the structure of the fixing metal fixture 25.

Figure 5A:
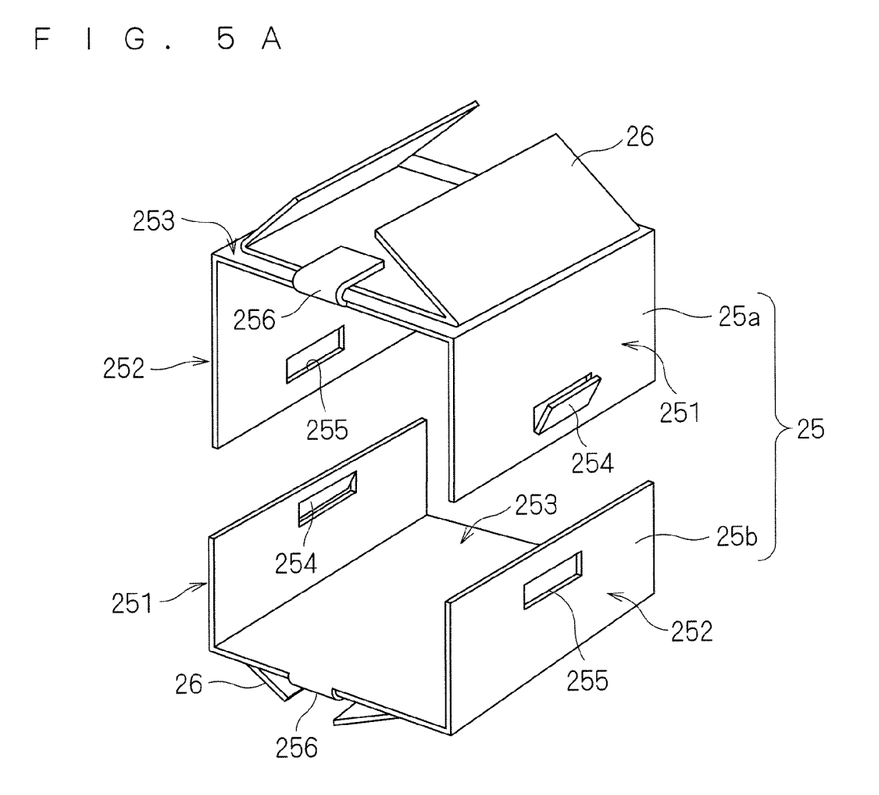
FIGS. 5A and 5B are perspective views showing a structure of a fixing metal fixture 25.
Figure 5B:
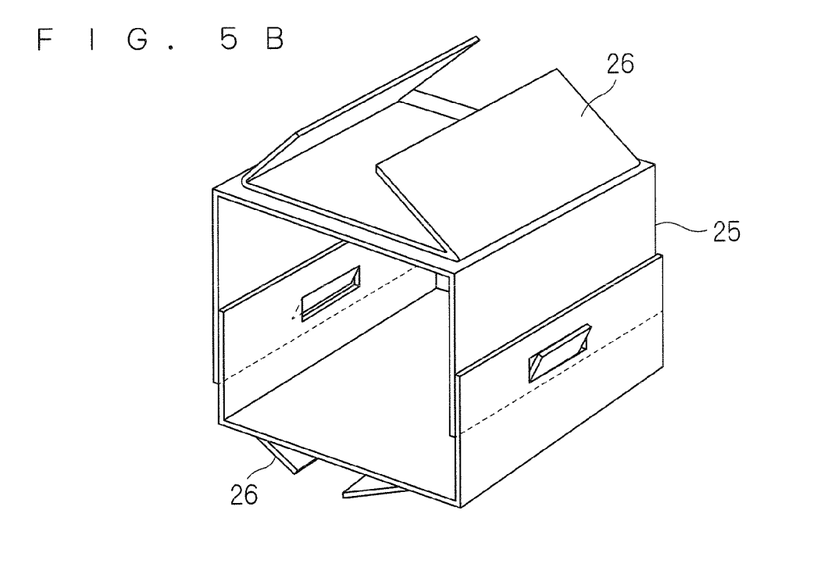

FIGS. 5A and 5B are perspective views showing a structure of the fixing metal fixture 25. FIG. 5A shows a state before assembling the first fixture member 25a and the second fixture member 25b, and FIG. 5B shows a state in which the first fixture member 25a and the second fixture member 25b are assembled.

The first fixture member 25a and the second fixture member 25b are the members having the same shape of approximately C-shaped form in a cross sectional view. In more detail, the first fixture member 25a and the second fixture member 25b have a structure in which a first side surface part 251 and a second side surface part 252 opposed to each other are connected vertically to an upper surface part 253. In this case, each of side surface parts of the first fixture member 25a and the second fixture member 25b is formed in such a manner as to be deformable in an elastic range having a line of intersection with the upper surface part 253 as an axis.

The first side surface part 251 is provided with an engaging part 254. The engaging part 254 is a protruding part which is provided in such a manner that a cut part of the C-shaped form is bent toward an outer side of the first side surface part 251 while having an end part side of the first side surface part 251 as a supporting point, so as to form an angle of about several degrees to the maximum with respect to the first side surface part 251. On the other hand, the second side surface part 252 is provided with an engaged part 255 which is a rectangular opening part with which the engaging part 254 can engage. In other words, it is said that a set of the engaging part 254 in one of the first fixture member 25a and the second fixture member 25b and the engaged part 255 of another of them form one engaging mechanism. That is, this can be said that the fixing metal fixture 25 have two sets of engaging mechanisms (a pair of engaging mechanism pairs).

Although an illustration is omitted in FIG. 4, the upper surface part 253 is structured such that the pressing spring 26 is retained by a pair of retaining parts 256 (in this case, only one part of which is illustrated in FIGS. 5A and 5B). In the case of the present embodiment, the upper surface part 253 is previously provided with an extending part (retaining part 256) which extends from itself at its end part, and a lower base part of the pressing spring 26 is pinched between the upper surface part 253 and the extending part by folding back the extending part, thereby retaining the pressing spring 26. However, a retaining aspect of the pressing spring 26 by the fixing metal fixture 25 is not limited to this.

If the first fixture member 25a and the second fixture member 25b having the structure mentioned above are arranged in a point symmetrical manner in a cross sectional view as shown in FIG. 5A, and the respective engaging parts 254 are engaged with the engaged parts 255 in another by moving both close to each other, the fixing metal fixture 25 in which the first fixture member 25a and the second fixture member 25b are combined as shown in FIG. 5B is constructed. In this case, since each of the side surface parts of the first fixture member 25a and the second fixture member 25b is formed so as to be elastically deformable, the engagement can be easily achieved. The assembly of the fixing metal fixture 25 shown in the state (d) in FIG. 4 is achieved by carrying out an engagement shown in FIG. 5B in a state that the housing 24 is arranged therebetween. In other words, it can be said that the fixing metal fixture 25 functions as a constraint member constraining the housing member 24a owing to this engaged state.

Figures 6A, 6C:
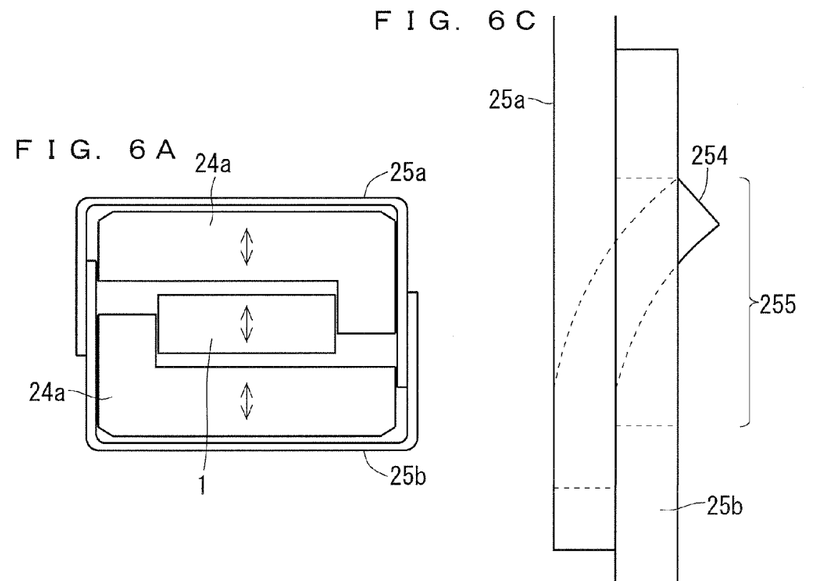
FIGS. 6A to 6D are views schematically showing a state of the fixing metal fixture 25 before and after a caulking ring 27 is caulked.
Figures 6B, 6D:
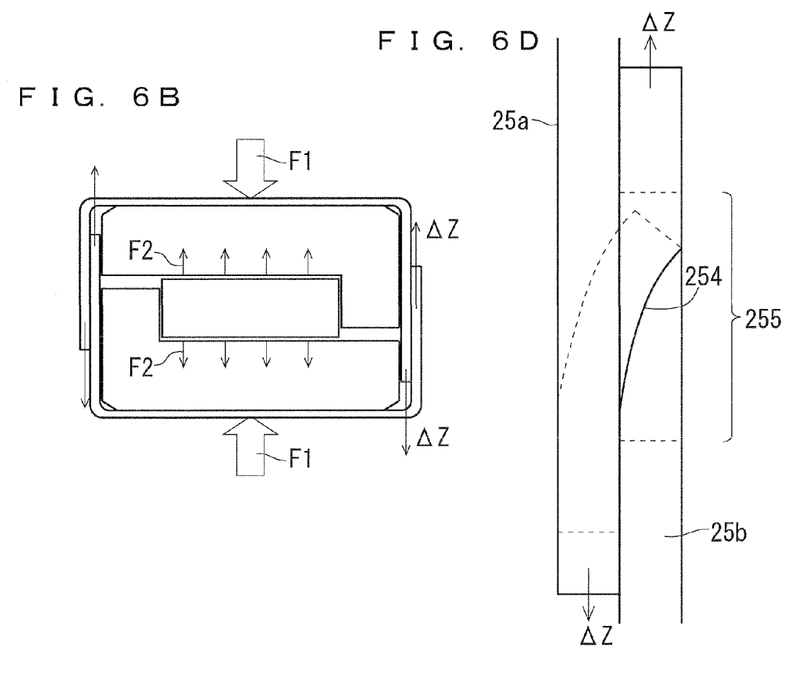

FIGS. 6A to 6D are views schematically showing a state of the fixing metal fixture 25 before and after, in the case that the caulking ring 27 is caulked for integrating the gas sensor main body 10 and the contact member 20. In this case, in order to simplify an illustration, the contact point member 21, the pressing spring 26 and the caulking ring 27 are omitted. FIG. 6A is a cross sectional view of the contact member 20 showing a state before the caulking ring 27 is caulked, and FIG. 6B is a cross sectional view of the contact member 20 showing a state after the caulking ring 27 is caulked. Further, FIGS. 6C and 6D are partly enlarged views of the fixing metal fixture 25 in the respective cases.

Until the caulking ring 27 is caulked, the first fixture member 25a and the second fixture member 25b are combined, with the respective engaging parts 254 being engaged with the engaged parts 255 in another, as shown in FIG. 6C. At this time, as shown in FIG. 6A, the fixing metal fixture 25 functions as a constraint member, and constrains the housing member 24a and the second element 1, however, the housing member 24a and the sensor element 1 are not completely fixed, but can displace within a certain range.

On the other hand, once the caulking ring 27 is caulked, an elastic force F1 is generated in the pressing spring 26 since a free end part 261 is in contact with the caulking ring 27, and the elastic force F1 acts on the fixing metal fixture 25 as a force in a direction of compressing it, as shown in FIG. 6B. In accordance with this, the first fixture member 25a and the second fixture member 25b displace in a direction of coming close to each other (a displacement of the first fixture member 25a and the second fixture member 25b at this time is set to Δz). Accordingly, the contact point member attached to the housing member 24a comes into contact with the sensor element 1, and the sensor element 1 is pinched and fixed by a pair of housing members 24a in such a manner that the elastic force F1 mentioned above goes with a drag F2 acting as a reaction force of the elastic force which the sensor element 1 receives from the contact point member 21 (accurately, a sum of the drags F2 from the individual contact point members 21).

At this time, each of the first fixture member 25a and the second fixture member 25b displaces at Δz, however, in the fixing metal fixture 25, as shown in FIG. 6D, the engagement of the engaging part 254 of each of the first fixture member 25a and the second fixture member 25b with respect to the engaged part 255 of the other is released, in accordance with the displacement mentioned above. Thus, after the caulking ring 27 is caulked, the first fixture member 25a and the second fixture member 25b turns to a non-engaged state so as to be simply pinched by the pressing spring 26 and the caulking ring 27. In other words, the elastic force F1 from the pressing spring 26 is directly applied to the housing member 24a regardless of the constraint by the fixing metal fixture 25. This means that a constraining function by the fixing metal fixture 25 is made so as to be disabled after the caulking ring 27 is caulked. As a result, an elastic force uniformly acts on the sensor element 1 from the individual contact point member 21. Of course, this is equivalent to a matter that the drag F2 uniformly acts.

Figure 7A:
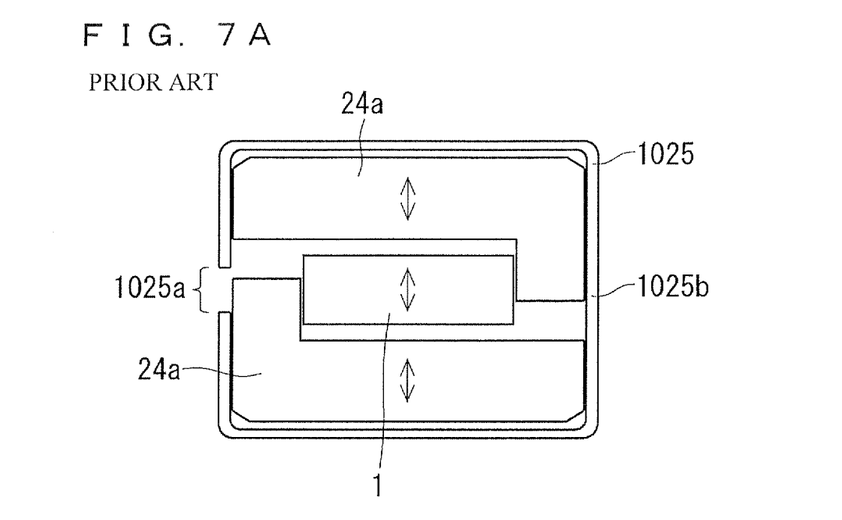
FIGS. 7A and 7B are views schematically showing a state of a conventional fixing metal fixture 1025 formed as a C-shaped form in a cross section in use before and after the caulking ring 27 is caulked.
Figure 7B:
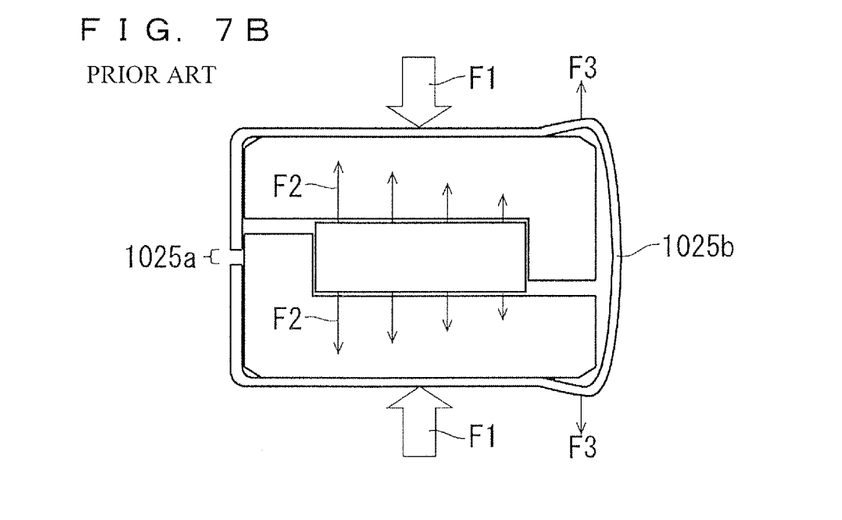

FIGS. 7A and 7B are views schematically showing a state of a conventional fixing metal fixture 1025 having a C-shaped form in a cross section in use before and after caulking the caulking ring 27 for comparison.

As shown in FIG. 7A, the fixing metal fixture 1025 is structured such that a gap 1025a is formed by making one side open, however, a side opposing to the gap 1025a is a fixed end 1025b. In a state before the caulking, in the same manner as the present embodiment, the housing member 24a and the sensor element 1 are constrained by the conventional fixing metal fixture 1025, however, the housing member 24a and the sensor element 1 can displace in a certain range.

On the other hand, once the caulking ring 27 is caulked, and the elastic force F1 is applied from the pressing spring 26, the gap 1025a becomes smaller in the fixing metal fixture 1025, and a deformation is generated in the side of the fixing end 1025b, as shown in FIG. 7B. In accordance with this, the elastic force which the sensor element 1 receives from the contact point member 21 and the drag F2 thereof become non-uniform which are different in the individual contact point members 21, and a reaction force F3 with respect to the deformation is generated in the fixing metal fixture 1025 itself. Accordingly, the contact state between the contact point member 21 and the electrode terminal 1a of the sensor element 1 does not become uniform. In some cases, contact point defect is generated.

On the contrary, in the present embodiment, although the fixing metal fixture 25 constrains the housing member 24a and the sensor element 1 before caulking as mentioned above, it does not generate any reaction force at a time of caulking. This is why a non-uniformity depending on the location does not occur in the contact state between the contact point member 21 and the electrode terminal 1a of the sensor element 1. That is, a stable contact state can be securely achieved by using the fixing metal fixture 25 in accordance with the present embodiment.

Further, it can be said that it results in the operation and effect mentioned above specifically to construct the fixing metal fixture 25 by the first fixture member 25a and the second fixture member 25b having such the structure that they can be engaged with each other before being caulked but their the engagement is released after caulking.

As mentioned above, in accordance with the present embodiment, it is possible to securely achieve a uniform and stable contact state between the contact point member of the contact member and the electrode terminal of the sensor element by using the fixing metal fixture which constrains the housing member and the sensor element in the inner side thereof before caulking, however, having the constraining function being made to be disabled after caulking.

Modified Embodiment

Figure 8A:
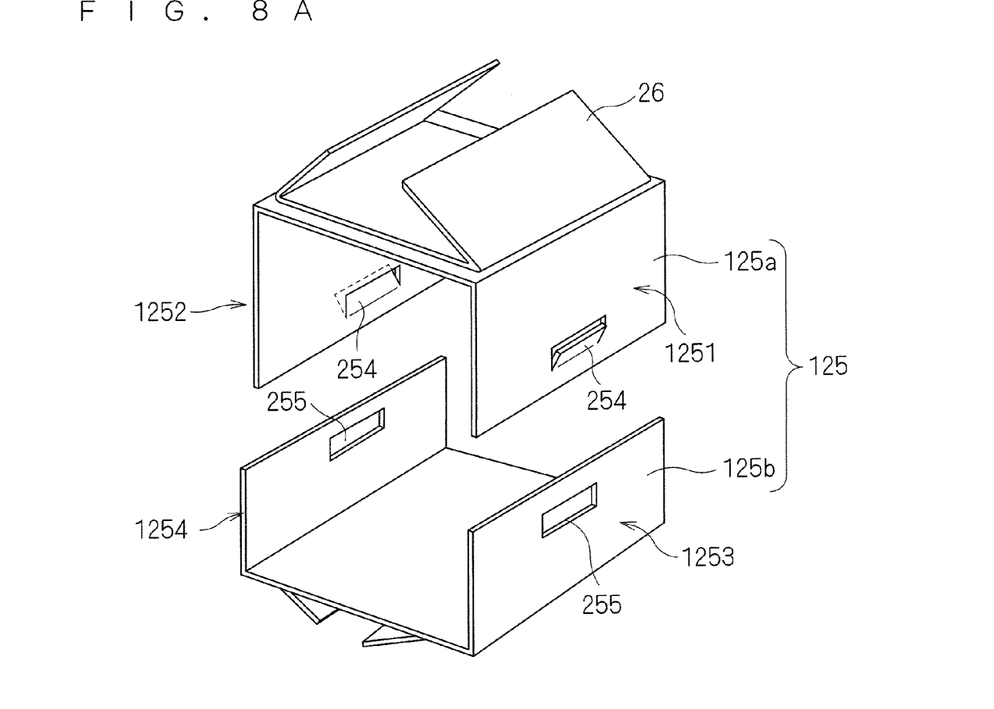
FIGS. 8A and 8B are perspective views schematically showing a structure of a fixing metal fixture in accordance with a modified embodiment.
Figure 8B:
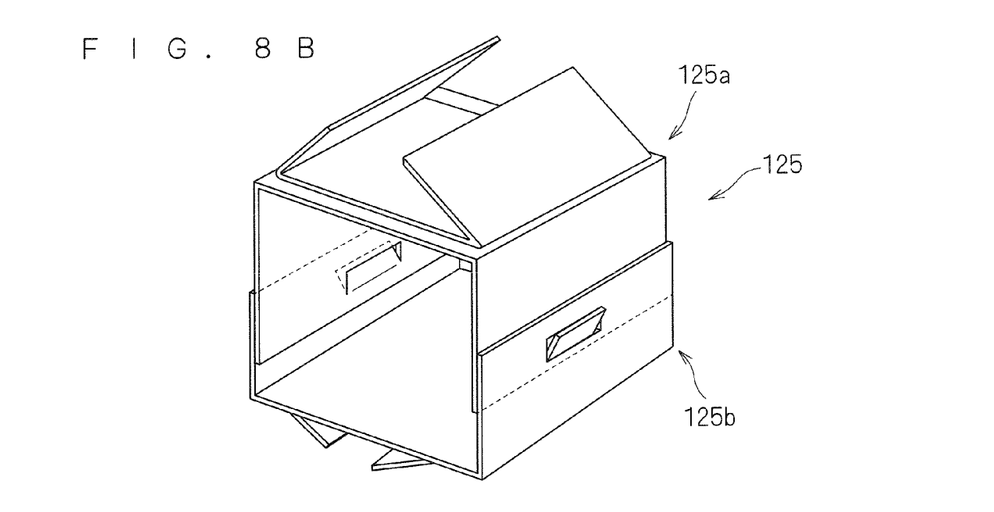
Figure 9A:
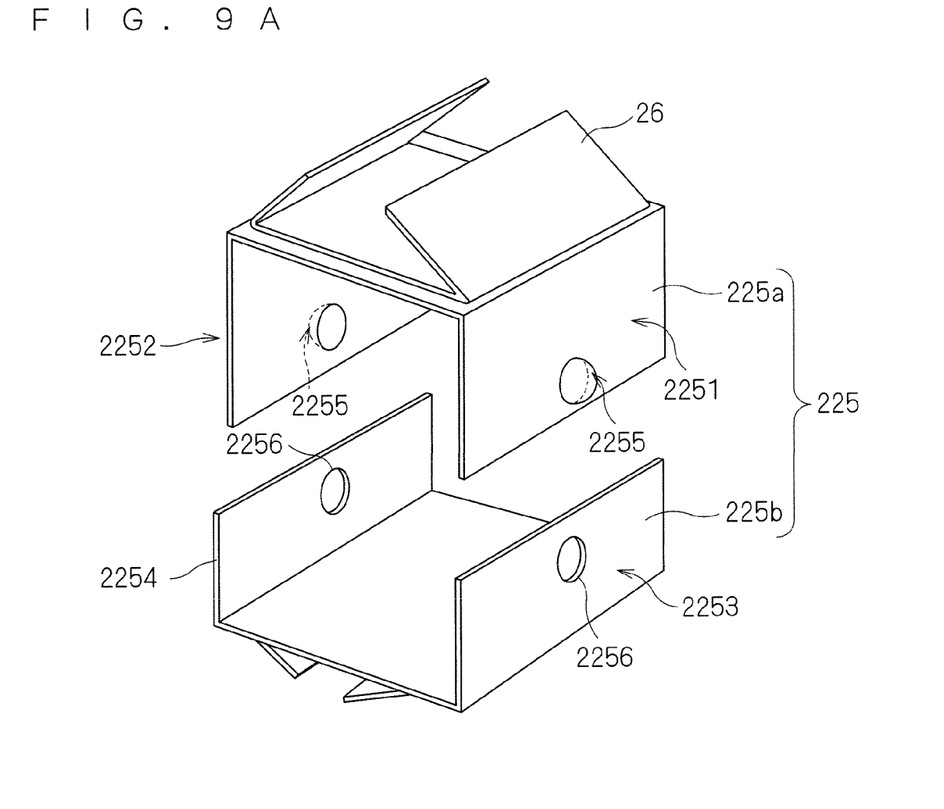
FIGS. 9A and 9B are perspective views schematically showing a structure of a fixing metal fixture in accordance with a modified embodiment.
Figure 9B:
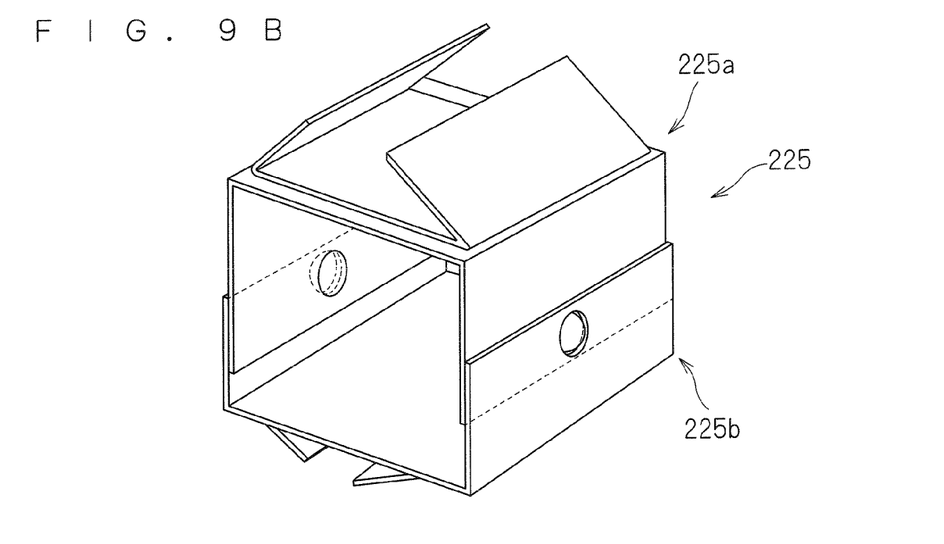
Figure 10A:
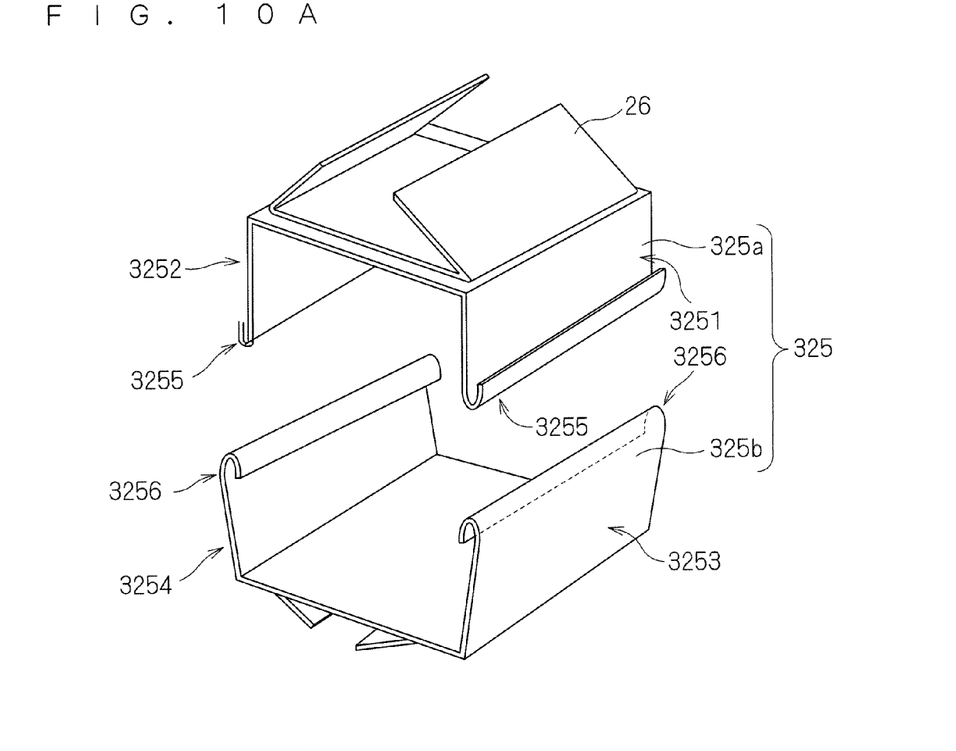
FIGS. 10A and 10B are perspective views schematically showing a structure of a fixing metal fixture in accordance with a modified embodiment.
Figure 10B:
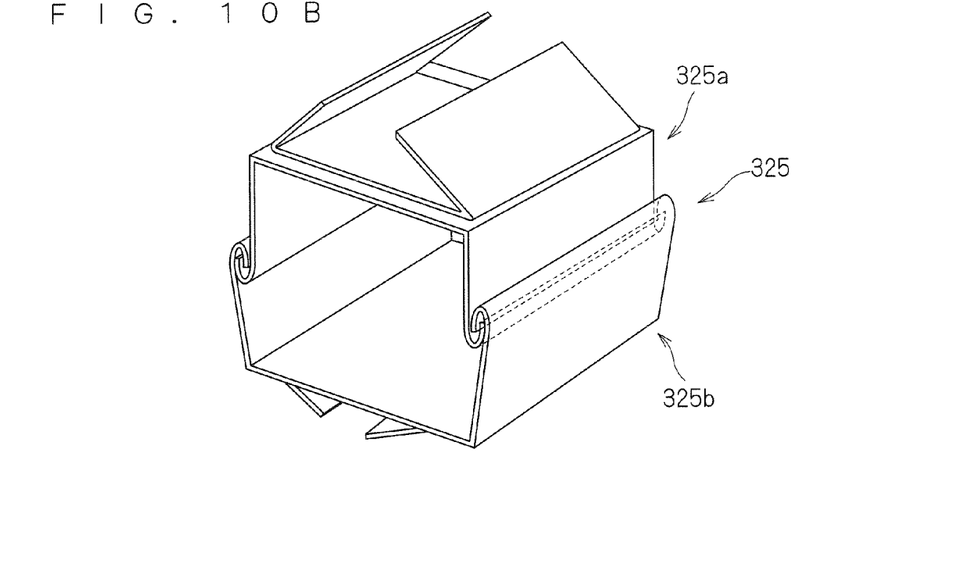

The structure of the fixing metal fixture achieving the operation and effect mentioned above is not limited to that shown in the embodiment mentioned above. FIGS. 8A, 8B, 9A, 9B, 10A and 10B are perspective views schematically showing structures of fixing metal fixtures in accordance with various modified embodiments. In the drawings, FIGS. 8A, 9A, and 10A show a non-engaged state, and FIGS. 8B, 9B, and 10B show an engaged state. All of the fixing metal fixtures shown in FIGS. 8A, 8B, 9A, 9B, 10A, and 10B are in common with the embodiment mentioned above, in that each of them is constructed by the first fixture member and the second fixture member which have approximately the C-shaped form in the cross sectional view.

The fixing metal fixture 125 shown in FIGS. 8A and 8B is structured such that the same engaging part 254 as the embodiment mentioned above is provided in both of a first side surface part 1251 and a second side surface part 1252 of the first fixture member 125a, and the same engaged part 255 as the embodiment mentioned above is provided in both of a first side surface part 1253 and a second side surface part 1254 of the second fixture member 125b, in accordance with the engaging part 254 in each of the first fixture members 1251a. In other words, the fixing metal fixture 125 is different from the fixing metal fixture 25 in that the first fixture member 125a and the second fixture member 125*b* have the different shapes, whereas two fixture members have the same shape in the fixing metal fixture 25.

However, the fixing metal fixture 125 having the structure mentioned above is the same as the fixing metal fixture 25 in that the engaged state is established by engaging the engaging part 254 in each of the first fixture members 125*la* with the corresponding engaged part 255 in the second fixture member 125*b*, and the non-engaged state is established by releasing the engagement by the application of the force compressing in the vertical direction. Accordingly, in the case that the fixing metal fixture 125 mentioned above is used for the preliminary assembly of the contact member 20, it is possible to obtain the same operation and effect as the case of using the fixing metal fixture 25.

A fixing metal fixture 225 shown in FIGS. 9A and 9B is structured such that an engaging part 2255 formed as a semispherical shape is provided in both of a first side surface part 2251 and a second side surface part 2252 of a first fixture member 225*a*, and a circular engaged part 2256 is provided in both of a first side surface part 2253 and a second side surface part 2254 of a second fixture member 225*b* in accordance with the respective engaging parts 2255 of the first fixture member 2251*a*. In other words, the fixing metal fixture 225 is different from the fixing metal fixtures 25 and 125 in the structure for engaging two members.

The fixing metal fixture 225 having the structure mentioned above is the same as the fixing metal fixtures 25 and 125 in that the engaged state is established by engaging the engaging part 2255 in each of the first fixture members 225*a* with the corresponding engaged part 2256 in the second fixture member 225*b*, and the non-engaged state is established by releasing the engagement by the application of the force compressing in the vertical direction. In this case, the engagement between the engaging part 2255 and the engaged part 2256 can be easily achieved by setting each of the side surface parts of the first fixture member 225*a* and the second fixture member 225*b* so as to be elastically deformable in the same manner as the fixing metal fixture 25. Accordingly, even in the case that the fixing metal fixture 225 mentioned above is used for the preliminary assembly of the contact member 20, it is possible to obtain the same operations and effects as the case of using the fixing metal fixture 25.

In the fixing metal fixture 225, the engaging part 2255 is provided only in the first fixture member 225*a*, and the engaged part 2256 is provided only in the second fixture member 225*b*, however, in place of this, two members having the same shape may be used as the first fixture member and the second fixture member, in the same manner as the fixing metal fixture 25 in accordance with the embodiment mentioned above. That is, two members each of which is provided with the engaging part 2255 in one side surface part, and the engaged part 2256 in another side surface part may be prepared, and they may be respectively defined as the first fixture member and the second fixture member.

A fixing metal fixture 325 shown in FIGS. 10A and 10B are structured such that an engaging part 3255 is provided in end parts of both of a first side surface part 3251 and a second side surface part 3252 of a first fixture member 325*a*, and an engaged part 3256 is provided in end parts of both of a first side surface part 3253 and a second side surface part 3254 of a second fixture member 325*b* in accordance with the respective engaging parts 3255 of the first fixture member 3251*a*. In other words, even in the fixing metal fixture 325, the structure for engaging two members is different from the fixing metal fixtures 25 and 125.

Specifically, the engaging part 3255 provided in the first fixture member 325*a* has such a shape that the end parts of both of the first side surface part 3251 and the second side surface part 3252 are bent to an outer side so as to form an approximately U-shaped form in a cross section, and the engaged part 3256 provided in the second fixture member 325*b* has such a shape that the end parts of both of the first side surface part 3253 and the second side surface part 3254 are bent to an inner side so as to form an approximately U-shaped form in a cross section.

The fixing metal fixture 325 having the structure mentioned above is the same as the fixing metal fixtures 25 and 125 in that the engaged state is established by engaging the respective engaging part 3255 of the first fixture member 325*a* with the corresponding engaged parts 3256 of the second fixture member 325*b*, and the non-engaged state is established on the basis of the application of the force compressing in the vertical direction. In this case, the engagement between the engaging part 3255 and the engaged part 3256 can be easily achieved by setting each of the side surface parts of the first fixture member 325*a* and the second fixture member 325*b* so as to be elastically deformable in the same manner as the fixing metal fixture 25. Accordingly, even in the case that the fixing metal fixture 325 mentioned above is used for the preliminary assembly of the contact member 20, it is possible to obtain the same operations and effects as the case of using the fixing metal fixture 25.

In this case, in the fixing metal fixture 325, the engaging part 3255 is provided only in the first fixture member 325*a*, and the engaged part 3256 is provided only in the second fixture member 325*b*, however, in place of this, two members having the same shape may be used as the first fixture member and the second fixture member, in the same manner as the fixing metal fixture 25 in accordance with the embodiment mentioned above. In other words, two members each of which is provided with the engaging part 3255 in one side surface part, and the engaged part 3256 in another side surface part may be prepared, and they may be respectively defined as the first fixture member and the second fixture member.

The invention claimed is:

1. A contact member for a gas sensor in which an electric connection to a sensor element is obtained by pinching and fixing said sensor element in an inserting port formed by a pair of housing members, comprising:

a constraint member which is provided so as to surround an outer periphery of said pair of housing members and has a constraining function of constraining a displacement of said pair of housing members within a predetermined range; and an annular member which is provided in an outer periphery of said constraint member, wherein said pair of housing members and said sensor element are brought into pressure contact, and said sensor element is pinched and fixed by said pair of housing members in a state that an electrode terminal provided in said sensor element comes into contact with a contact point member provided in said pair of housing members, due to contractive deformation of said annular member with receiving an external force in a state that said sensor element is inserted in said insertion port, said constraint member constrains a displacement of said pair of housing members within a predetermined range before said sensor element is pinched and fixed by said pair of housing members, and exists in a state of being pinched between said annular member and said pair of housing members without generating any reaction force with respect to said external force, after said sensor element is pinched and fixed, said constraint member is constructed by a first member and a second member, said constraint member is provided with two sets of engaging mechanisms which engage said first member and said second member, each of said two sets of engaging mechanisms is constructed by an engaging part which is provided in one of said first member and said second member and an engaged part which is provided in the other, the engagement of said first member and said second member causes the constraint of said pair of housing members with said constraint member such that said pair of housing members and sensor element can move within the predetermined range, and said two sets of engaging mechanisms are disengaged when said sensor element is pinched and fixed.

2. The contact member for the gas sensor according to claim 1, wherein each of said first member and said second member is provided with one engaging part and one engaged part of said two sets of engaging mechanisms.

3. The contact member for the gas sensor according to claim 2, wherein said first member and said second member are members having approximately the same shape.

4. The contact member for the gas sensor according to claim 1, wherein said engaging parts of both of said two sets of engaging mechanisms are provided in one of said first member and said second member, and said engaged parts of both of said two sets of engaging mechanisms are provided in the other of said first member and said second member.

5. A connecting method of a sensor element of a gas sensor and a contact member, comprising:
- a step of preparing a contact member that comprises
  - a pair of housing members which are arranged to form an insertion port in which the sensor element is inserted,
  - a constraint member which is provided so as to surround an outer periphery of said pair of housing members, and has a constraining function of constraining a displacement of said pair of housing members within a predetermined range, and
  - an annular member which is provided in an outer periphery of said constraint member;
- a step of inserting said sensor element in said insertion port; and
- a step of bringing said pair of housing members into pressure contact with said sensor element by applying an external force to said annular member to deform said annular member so as to contract, thereby pinching and fixing said sensor element in said pair of housing members in a state that an electrode terminal provided in said sensor element is brought into contact with a contact point member provided in said pair of housing members, wherein said constraint member constrains a displacement of said pair of housing members within a predetermined range before said sensor element is pinched and fixed by said pair of housing members, and exists in a state of being pinched between said annular member and said pair of housing members without generating any reaction force with respect to said external force, after said sensor element is pinched and fixed, said constraint member is constructed by a first member and a second member, said constraint member is provided with two sets of engaging mechanisms which engage said first member and said second member, each of said two sets of engaging mechanisms is constructed by an engaging part which is provided in one of said first member and said second member and an engaged part which is provided in the other, the engagement of said first member and said second member causes the constraint of said pair of housing members with said constraint member such that said pair of housing members and sensor element can move within the predetermined range, and said two sets of engaging mechanisms are disengaged when said sensor element is pinched and fixed.

6. A manufacturing method of a gas sensor comprising:
- a step of arranging a pair of housing members in a state of forming an inserting port in which a sensor element is inserted;
- a step of providing a constraint member having a constraining function of constraining a displacement of said pair of housing members within a predetermined range, said constraint member provided so as to surround an outer periphery of said pair of housing members;
- a step of providing an annular member in an outer periphery of said constraint member;
- a step of inserting said sensor element in said insertion port; and
- a step of bringing said pair of housing members into pressure contact with said sensor element by applying an external force to said annular member to deform said annular member so as to contract, thereby pinching and fixing said sensor element in said pair of housing members in a state that an electrode terminal provided in said sensor element is brought into contact with a contact point member provided in said pair of housing members, wherein said constraint member constrains a displacement of said pair of housing members within a predetermined range before said sensor element is pinched and fixed by said pair of housing members, and exists in a state of being pinched between said annular member and said pair of housing members without generating any reaction force with respect to said external force, after said sensor element is pinched and fixed, said constraint member is constructed by a first member and a second member, said constraint member is provided with two sets of engaging mechanisms which engage said first member and said second member, each of said two sets of engaging mechanisms is constructed by an engaging part which is provided in one of said first member and said second member and an engaged part which is provided in the other, the engagement of said first member and said second member causes the constraint of said pair of housing members with said constraint member such that said pair of housing members and sensor element can move within the predetermined range, and said two sets of engaging mechanisms are disengaged when said sensor element is pinched and fixed.

* * * * *